(12) United States Patent
Mitragotri et al.

(10) Patent No.: US 10,618,983 B2
(45) Date of Patent: Apr. 14, 2020

(54) HYALURONIC ACID-BASED HYDROGELS HAVING MEDICAL APPLICATIONS

(71) Applicant: The Regents of the University of California, Oakland, CA (US)

(72) Inventors: Samir Mitragotri, Santa Barbara, CA (US); Stefano Menegatti, Raleigh, NC (US)

(73) Assignee: The Regents of the University of California, Oakland, CA (US)

( * ) Notice: Subject to any disclaimer, the term of this patent is extended or adjusted under 35 U.S.C. 154(b) by 120 days.

(21) Appl. No.: 15/580,671

(22) PCT Filed: Jun. 11, 2016

(86) PCT No.: PCT/US2016/037100
§ 371 (c)(1),
(2) Date: Dec. 7, 2017

(87) PCT Pub. No.: WO2016/201382
PCT Pub. Date: Dec. 15, 2016

(65) Prior Publication Data
US 2018/0186900 A1 Jul. 5, 2018

Related U.S. Application Data

(60) Provisional application No. 62/174,171, filed on Jun. 11, 2015.

(51) Int. Cl.
| | | |
|---|---|---|
| C08B 37/00 | (2006.01) | |
| C08B 37/08 | (2006.01) | |
| A61L 27/20 | (2006.01) | |
| A61L 27/52 | (2006.01) | |
| A61L 27/54 | (2006.01) | |
| A61L 27/38 | (2006.01) | |
| A61K 45/06 | (2006.01) | |
| C08J 3/075 | (2006.01) | |
| C08L 5/08 | (2006.01) | |
| A61K 31/728 | (2006.01) | |
| A61M 5/19 | (2006.01) | |
| A61M 5/315 | (2006.01) | |
| C07K 16/28 | (2006.01) | |
| A61K 9/00 | (2006.01) | |
| A61K 9/06 | (2006.01) | |
| A61K 47/36 | (2006.01) | |

(52) U.S. Cl.
CPC ........ *C08B 37/0072* (2013.01); *A61K 31/728* (2013.01); *A61K 45/06* (2013.01); *A61L 27/20* (2013.01); *A61L 27/38* (2013.01); *A61L 27/52* (2013.01); *A61L 27/54* (2013.01); *A61M 5/19* (2013.01); *A61M 5/31596* (2013.01); *C07K 16/283* (2013.01); *C08J 3/075* (2013.01); *C08L 5/08* (2013.01); *A61K 9/0014* (2013.01); *A61K 9/06* (2013.01); *A61K 47/36* (2013.01); *A61L 2300/402* (2013.01); *A61L 2300/406* (2013.01); *A61L 2300/414* (2013.01); *A61L 2300/436* (2013.01); *A61L 2400/06* (2013.01); *A61M 2210/04* (2013.01)

(58) Field of Classification Search
CPC ........ C08B 37/0072; C08J 3/075; C08L 5/08; A61M 5/19; A61M 5/31596; C07K 16/283; A61K 31/728; A61K 45/06; A61K 9/06; A61K 9/0014; A61K 47/36; A61L 27/54; A61L 27/52; A61L 27/38; A61L 27/20; A61L 2300/436; A61L 2300/414; A61L 2300/406; A61L 2300/402; A61L 2400/06
See application file for complete search history.

(56) References Cited

U.S. PATENT DOCUMENTS

| | | |
|---|---|---|
| 2010/0291357 A1 | 11/2010 | Polizzotti et al. |
| 2013/0345319 A1 | 12/2013 | Messersmith et al. |
| 2014/0256831 A1 | 9/2014 | Ito et al. |

OTHER PUBLICATIONS

Wang et al., "Click Chemistry" for Molecular Imaging, Current Molecular Imaging, vol. 1, Nol. 1, pp. 87-95(9), Oct. 1, 2012.
Menegatti et al., "Synthesis and Characterization of a Self Fluorescent Hyaluronic Acid-Based Gel for Dermal Applications," Advanced Healthcare Materials, vol. 4, Issue 15, pp. 2297-2305. Sep. 2015.
X. Zhang et al.: "Improved method for synthesis of cysteine modified hyaluronic acid for in situ hydrogel formation". Chemical Communications. No. 51, May 11, 2015 (May 11, 2015). pp. 9662-9665. XP002787701. DOI: 10.1039/C5CC02367J * schemes 1 and 3; p. 9662. left-hand column. paragraph 1 * * p. 9664. right-hand column *.
Application No. 16808484.6, corresponding European application, European Search Report, dated Jan. 30, 2019, 9 pages.

*Primary Examiner* — Robert S Jones

(57) ABSTRACT

Provided herein are novel hyaluronic acid-based materials for in-situ gelation in wounds and other contexts, which materials are biocompatible and which have favorable gelation kinetics. The resulting hydrogels have desirable rheological properties. The invention encompasses novel reagents for forming crosslinked hyaluronic acid hydrogels, with favorable kinetics for medical applications and having desirable and tunable physical properties. Also presented herein are methods of using the novel materials disclosed herein in wound care and other medical contexts.

11 Claims, 3 Drawing Sheets

HYALURONIC ACID-BASED HYDROGELS HAVING MEDICAL APPLICATIONS

CROSS-REFERENCE TO RELATED APPLICATIONS

This application claims priority to International Patent Application Number PCT/US2016/37100, entitled "Novel Hyaluronic Acid-Based Hydrogels Having Medical Applications," filed on Jun. 11, 2016, which claims priority to U.S. Provisional Patent Application No. 62/174,171, entitled "Novel Hyaluronic Acid-Based Hydrogels Having Medical Applications," filed on Jun. 11, 2015, each of which is incorporated by reference herein in its entirety.

BACKGROUND OF THE INVENTION

Polymer-based systems capable of in situ gelation are potentially useful in treating surgical or traumatic disruption of organs, connective tissue, muscles, tendons and membranes. Injectable materials that can effectively seal or suture internal wounds (e.g., needle holes, necrotic spaces, arthritic cavities) to achieve tissue approximation for better wound healing would be desirable. Such systems must meet five crucial requirements: safety, efficacy, usability, cost, and regulatory approval. In particular, they must show adequate adhesion with underlying tissue, biocompatibility and biodegradability, and shelf stability. Among the available United States FDA-approved materials, hyaluronic acid (HA) holds a prominent role. The HA present in living organisms is found primarily in extracellular and pericellular matrices, is highly hydrated, biocompatible, and non-immunogenic. These features, along with its degradability by native enzymes (hyaluronidases), make it potentially useful as a matrix component or visco-supplementation element in regenerative medicine.

Injectable HA-based materials can be filled into defects of any shape and cross-linked in situ. Known cross-linkable HA materials show good adhesion to the native tissues, affording good physicochemical interlocking and a cohesive polymer-tissue interface. A number of chemistries have been employed to design in situ gelable HA-based materials, such as: Schiff reaction between amine and aldehyde groups (for example as described in Tan, H., et al., Controlled gelation and degradation rates of injectable hyaluronic acid-based hydrogels through a double crosslinking strategy. J Tissue Eng Regen Med, 2011. 5(10): p. 790-7); Michael-type addition between thiols and diacrylates or other Michael-type acceptors (for example as described in Dong, Y., et al., Thermoresponsive hyperbranched copolymer with multi acrylate functionality for in situ cross-linkable hyaluronic acid composite semi-IPN hydrogel. J Mater Sci Mater Med, 2012. 23(1): p. 25-35); nucleophilic substitutions on haloacetates (for example as described in Serban, M. A. and G. D. Prestwich, Synthesis of hyaluronan haloacetates and biology of novel cross-linker-free synthetic extracellular matrix hydrogels. Biomacromolecules, 2007. 8(9): p. 2821-8; formation of disulphide bridges (for example as described in Shu, X. Z., et al., Disulfide-crosslinked hyaluronan-gelatin hydrogel films: a covalent mimic of the extracellular matrix for in vitro cell growth. Biomaterials, 2003. 24(21): p. 3825-34; free radical photopolymerization upon (meth) acrylic residues (for example as described in Park, Y. D., N. Tirelli, and J. A. Hubbell, Photopolymerized hyaluronic acid-based hydrogels and interpenetrating networks. Biomaterials, 2003. 24(6): p. 893-900; Huygens "click" reactions between azides and alkynes; and phenols (tyramines) that spontaneously cross-link after their enzymatic oxidation to catechols (for example as described in Jin, R., et al., Enzyme-mediated fast in situ formation of hydrogels from dextran-tyramine conjugates. Biomaterials, 2007. 28(18): p. 2791-800).

The previously known cross-linked matrices have been used in a variety of ways, from cartilage replacement and prevention of post-surgical issues to controlled release of biotherapeutics. These previously known modifications generally preserve HA sensitivity to hyaluronidases, thus allowing enzyme-mediated degradation of the hydrogels. However, the gelation kinetics and the biocompatibility of these previously developed reactive materials are not optimal. In some instances, the known HA modifications and reagents have shown some cytotoxicity. Another issue with the known compositions is presented by the kinetics, wherein in some cases gelation proceeds too quickly to enable proper filling of the target space before the gelation occurs. Gelation rate can in principle be controlled by acting on the amount of polymer precursor and/or cross-linker concentration. This, however, can adversely affect the mechanical properties of the resulting gel and hence its therapeutic value.

Therefore, there remains a continuing need in the art for HA-based in situ gelable systems capable of forming a resistant gel with slower kinetics, so as to enable a more homogeneous crosslinking and cavity filling, would be ideal for biomedical uses.

SUMMARY OF THE INVENTION

Provided herein are novel HA-based materials for in-situ gelation in wounds and other contexts, which materials are biocompatible and which have desirable gelation kinetics. The resulting hydrogels have desirable rheological properties. The invention encompasses novel reagents for forming crosslinked HA hydrogels, with favorable kinetics for medical applications and having desirable and tunable physical properties. Also presented herein are methods of using the novel materials disclosed herein in wound care and other medical contexts.

DETAILED DESCRIPTION OF THE INVENTION

Figure 1:
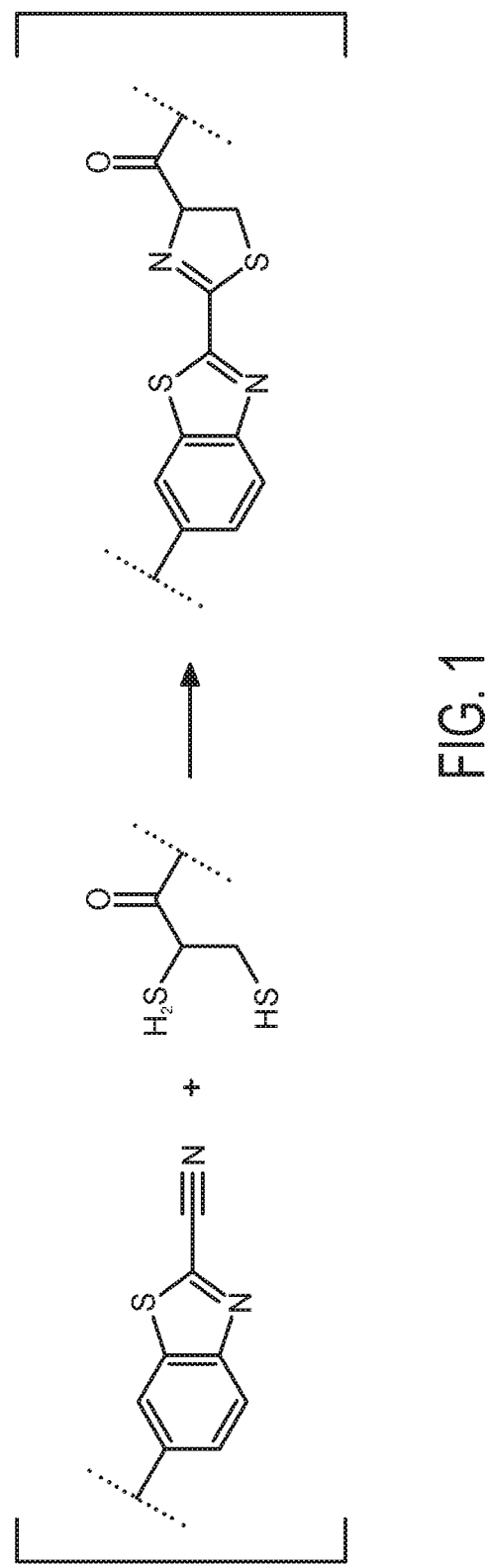
FIG. 1 depicts a liquid-phase "click" reaction between CBT and D-Cys. Dotted line represent a hyaluronoic acid polymer backbone.
Figure 2A:
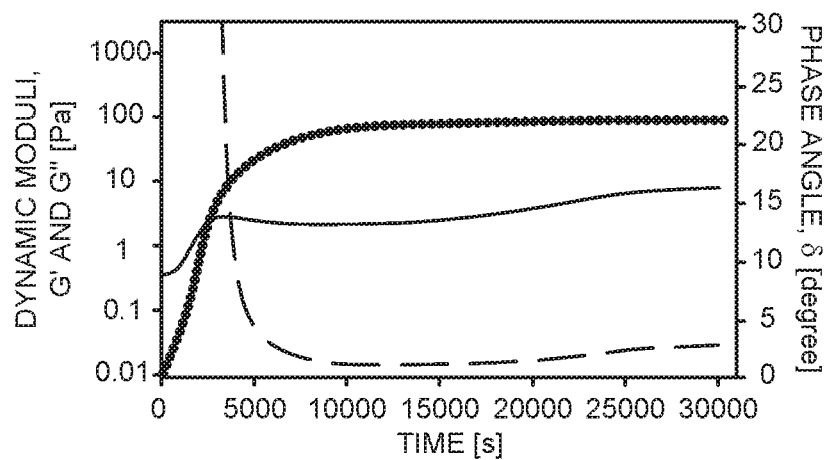
FIG. 2A depicts a dynamic oscillatory rheological characterization of a gel resulting by mixing an equimolar (5% mol) combination of HA-CBT and HA-D-Cys conjugates, both at 2% w/w in standard saline solution. Fig. B depicts a dynamic oscillatory rheological characterization of the gel.
Figure 2B:
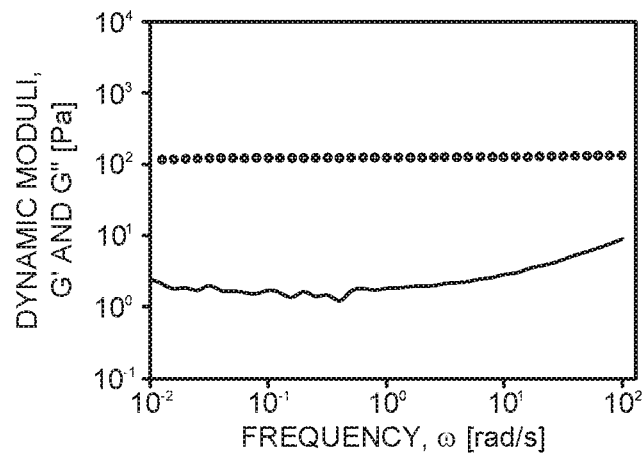
FIG. 2C depicts a steady-state shear viscosity of the gel as function of shear rate.
Figure 2C:
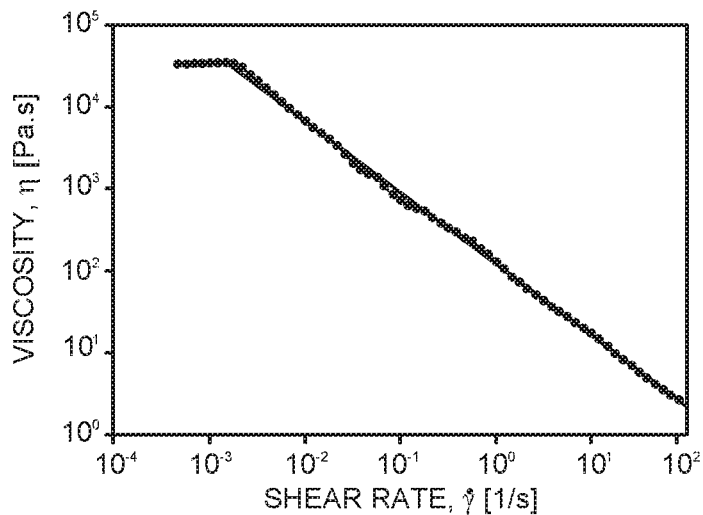
Figure 3:
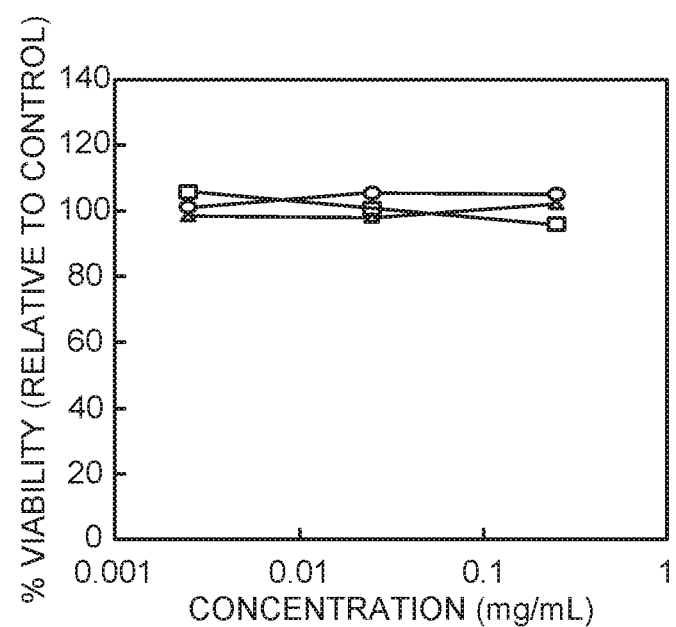
FIG. 3 depicts the viability of human epidermal keratinocytes after incubation with HA or HA-conjugates. HA (closed square), HA-CBT (closed circle), and HA-D-Cys (closed triangle). Error bars represent mean±SD for n=6.
Figure 4:
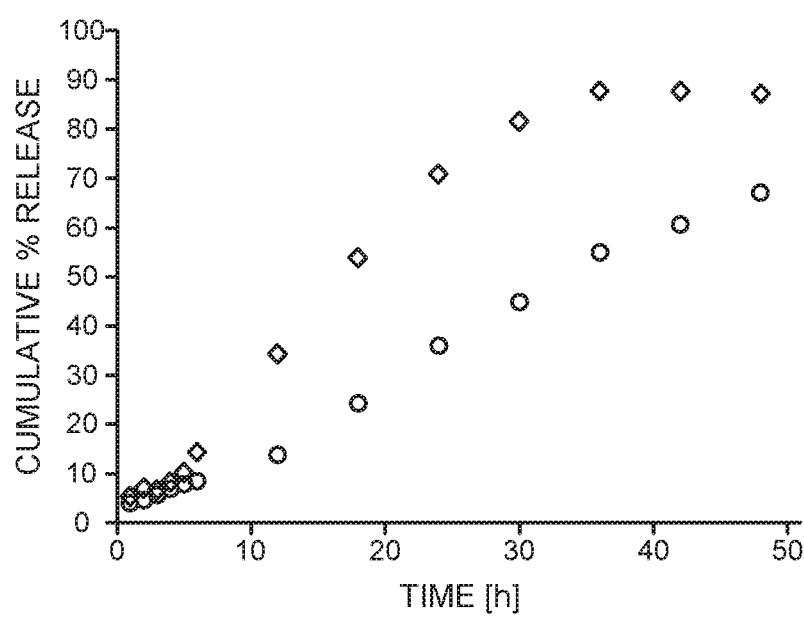
FIG. 4 depicts the release of BSA and IgG from a protein-loaded gel over 48 hours.

In a first aspect, the scope of the invention encompasses HA-based gelable systems. In one aspect, the invention encompasses methods of producing hydrogels in a space (such as a wound or a mold) using two complementary solutions of functionalized polymers, wherein resulting hydrogel forms with desirable kinetics which allow the space to properly fill and wherein the resulting hydrogel conforms to the boundaries of the space, is durable, biocompatible, and degradable. In another aspect, the invention encompasses kits comprising two vessels or compartments, wherein the two vessels or compartments hold solutions of functionalized polymers that, when mixed, will produce medically useful hydrogels with desirable kinetics. In another aspect, the scope of the invention encompasses the treatment of external or internal wounds with two complementary solutions of functionalized polymers, wherein the mixed solutions will form medically useful hydrogels with such formation having desirable kinetics. In another aspect, the scope of the invention encompasses a method of making medicament utilizing a pair of solutions, each solution comprising a complementary functionalized polymer, and said pair of solutions will form a hydrogel when mixed. The in situ gelable systems of the invention comprise various components, as follows.

Backbone Polymers

The compositions, kits, and methods described herein encompass the use of two solutions of functionalized polymers, which, when mixed, will create medically useful hydrogels. Various embodiments of the invention include functionalized HA polymers. The HA polymers utilized in the compositions of the invention may comprise HA polymers of any molecular weight, for example from 10-2,500 kDa. For example, in one embodiment, the HA polymers of the invention comprise HA polymers having a molecular weight of 200 to 300 kDa, for example a molecular weight of 250 kDa.

The scope of the invention further encompasses different polymers that can be used in place of HA, for example, natural polymers such as water soluble modified and non-modified polysaccharides, such as chitin and chitosan, alginate, starch, dextran, and pectin. Additionally, synthetic polymers may be used in place of HA as well, for example polyHPMA, polyvinylpyrrolidone co-polymerised with another polymer that allows coupling of the "click-able" moieties, polyvinylpyrrolidone, poly(N-isopropylacrylamide), poly(N,N-diethylacrylamide), poly(N-vinlycaprolactam), polyethylene glycol) co-polymerised with a polymer that allows coupling of the click-able moieties.

It will be understood that the functionalized polymers of the invention may comprise monodisperse, substantially homogeneous polymers, or may comprise polydisperse, mixed molecular-weight polymers.

The complementary solutions of the invention may comprise the same polymer. Alternatively, the complementary solutions may each comprise a different polymer species. In some embodiments, the polymer solutions comprise heterogeneous mixtures of functionalized polymers (e.g., two or more polymer species in a solution).

Cross-Linking Chemistry

The hydrogels of the invention are made by functionalizing two separate sets of polymers with complementary reactive groups, and subsequently mixing the two sets of functionalized polymers under conditions that will cause the reactive groups to condense, cross-linking the polymers and creating a hydrogel. The cross linking reactive groups of the invention comprise various pairs of complementary "click chemistry" groups that can readily form bonds under physiological conditions with favorable and tunable reaction kinetics and which form physiologically compatible gels. HA polymers, for example, are made up of alternating units of glucuronic acid and N-acetyl-glucosamine, each glucuronic acid unit displaying one carboxylic acid group to which reactive groups can be conjugated.

In one embodiment, the complementary cross-linking reactive groups utilized herein are cyanobenzothiazole (CBT) and D-cysteine (D-Cys). The click reaction between these two moieties is known in the art from other contexts, and plays a role in the light-producing mechanism in fireflies. Advantageously, the CBT and D-Cys condensation reaction avoids the formation of cytotoxic or irritating byproducts. L-cysteine may be substituted for D-cysteine.

Various modifications or substitutions of the CBT and D-Cys moieties may be made, as known in the art. For example, CBT-mimetics may be used in place of CBT. For example, nitriles (R-CN) can react with cysteine to form a dihydro-thiazole bond. For example, a nitrile group connected to a first through a covalent bond (the nitrile can also be the substituent on a moiety covalently linked on the polymer, such as a benzene ring, as in a benzonitrile) can react with D-Cys conjugated polymers (wherein D-Cys is connected to the polymer through a covalent bond), to form a dihydro-thiazole linkage. Notable examples are benzonitrile and cyanothiazole, the latter forming the same tether as CBT, but without the benzene ring fused to the thiazole.

Non-CBT mimetics that react with D-Cys may also be used in place of CBT, including molecules that react with either the —SH or the —NH$_2$ group of D-Cys. For example, a free —SH (thiol) group can react with the —SH group of D-Cys forming a disulphide bond. This bond, however, is readily hydrolized in reducing and alkaline conditions. Also, alkene moieties are reactive with —SH, via the so-called "Michael thiol-ene" addition. Furthermore, the —SH (thiol) group of D-Cys can be reacted with —COOH (carboxyl) to form thioester bonds. Likewise, —SH groups react with alkyl halides (e.g. dibromo/dichloro ethane) to form thio-ether bonds. The free-NH$_2$ (amino) group of D-Cys can also react with a variety of groups: carboxyl (to form an amide bond), aldehyde (to form an imine bond, converted to secondary amine bond by subsequent reduction), ketone (imine bond, converted to tertiary amine bond by subsequent reduction), alkyl halides (to form a secondary amine bond), as known in the art.

Mimetics of D-Cys that will also react with CBT may be used as the reactive group. D-Cys mimetics include (3R)-3-amino-4-sulfanylbutanoic acid, (4R)-4-amino-5-sulfanyl-pentanoic acid, and others known in the art.

Rheological Properties of the Hydrogels

In order to be useful in wound-filling and like applications, the hydrogels of the invention must have sufficient mechanical strength to withstand subcutaneous pressure while being flexible enough to move and deform naturally with surrounding tissues, so as to avoid damage to and to be comfortable for the patient. In general, a desirable hydrogel for wound filling will have rheological characteristics wherein G' (storage modulus, which describes the elastic—or solid-like-response of the material) is higher than G" (loss modulus, which described the viscous—or liquid-like—response of the material). In some embodiments, a G' between 1 and 2 orders of magnitude higher than G" is preferred. Further, for intracorporeal applications, a hydrogel having shear thinning properties (viscosity decreasing with shear rate) is desirable, so that when the gel is located in a space with moving boundaries, the gel becomes softer and the movement of the boundaries becomes more rapid, hence enabling the boundaries to move. A medically used hydrogel will also preferably recover its elastic properties when the motion of the boundaries decreases. Thus, more generally, it should be such that its viscosity undergoes ideal hysteresis cycles with the shear rate. It should also maintain its G' and G" ratio with the time and the mechanical stimuli, i.e. it should not degrade.

Reaction Kinetics

The kinetics of the crosslinking reaction is very important in the medical applications of the hydrogels. In wound care, the formation of a biocompatible hydrogel to fill holes, fissures, and other cavities, such as surgical incisions, necrotic or excised regions, and arthritic cavities is desired. Previously known HA-based hydrogels are formed using highly reactive groups and the hydrogels afforded by such materials are often formed too quickly for polymer mixture to fill the complex shape of the target cavity while gelation occurs. However, the novel hydrogel compositions of the invention advantageously have mild reaction kinetics, i.e., gelation does not occur too quickly, allowing the liquid precursor solution to infiltrate the complex and irregular geometries of real wounds, wherein they slowly form strong hydrogels precisely fitted to the target space, for example, gelation being complete in 15-45 minutes, for example in 30 minutes under physiological conditions (e.g., at pH 7.4 at 37° C.).

The gelation kinetics of hydrogel formation can be tuned by varying the amount of pendant reactive groups on the HA polymer backbones. For example, HA polymers functionalized at between 0.5 to 6.5% molar (as compared to the molar amount of carboxyl groups on HA) may be used, molar percentage or molar proportion being the percentage of carboxylic acids of the HA's which are modified with reactive groups. For example, HA polymers functionalized with about 5% molar reactive groups may be used. With increasing saturation of HA carboxyl groups by CBT, the polymer becomes less soluble, due to the hydrophobic nature of CBT. Above 6.5-7% CBT, the polymer becomes insoluble and is unfit for the formation of hydrogels. Rather than modifying the HA-CBT to make it more hydrophilic, if a higher saturation of reactive moieties is desired, a more hydrophilic CBT mimetic or substitute may be used. For D-Cys, increasing the concentration increases the degree of Cys-Cys reactions, forming disulphide bonds, which are not stable. Accordingly, in some implementations, D-Cyst concentrations above 10% are not preferred.

It will be understood that CBT mimetics, CBT substitutions, and modified forms of D-Cys may be utilized in place of CBT and D-Cys, and that the reactive groups of the HA polymers may comprise mixtures of three or more different reactive species.

In general, the percentage of reactive groups on the HA polymers will dictate the speed of the gelation process, with greater saturation by reactive groups potentially leading to faster gelation. However, it is understood that reaction kinetics are complex and may proceed in a non-linear manner. Likewise, as described above, the rheological properties of the resulting hydrogel are affected by the degree of reactive group saturation, with greater saturation leading to a stiffer gel.

Formation of Hydrogels

The complementary reactive functionalized polymers can be maintained in separate solutions and stored. The polymers-reactive group conjugates are stable in water, normal saline (e.g. about 0.9% saline) and in physiologically compatible buffers, such as PBS or other phosphate buffers with molarity between 10-150 mM.

The HA conjugates may be present in the solution at a concentration of 0.1 to 10 percent by weight (% w/w), for example, 5% w/w. In general more concentrated solutions will gel quickly while more dilute solutions will require longer time spans to gel, however the complexities of gelation mean this may not always be the case.

At the time of hydrogel formation, the two complementary solutions of functionalized polymers can be mixed and then applied to the target vessel, mold, surface, or cavity. It will generally be desirable to quickly (in a matter of seconds, for example) premix the solutions before injection or flow into the target space to avoid interfaces that prevent in-situ mixing. In one embodiment, the invention comprises any apparatus capable of storing two solutions separately and, upon a user's action, dispensing the two solutions in an admixed state. For example, the apparatus may comprise a dual-barreled syringe, optionally having a mixing chamber or mixing dispenser tip, wherein the complementary functionalized solutions may be stored separately in the two barrels and subsequently expelled in a mixed form. In another embodiment, the invention comprises a kit comprising a first solution of polymers functionalized with a first reactive group and a second solution of polymers functionalized with a second reactive group, wherein the first and second reactive groups are capable of forming bonds when in contact with one another, for example the first and second reactive groups comprising CBT and D-Cys.

Hydrogel formation kinetics may be altered by the co-administration of energy to accelerate cross-linking bond formation. Exemplary energy sources that may be utilized to accelerate gelation kinetics include electrical, mechanical, acoustic or thermal energy.

Medical Applications of the Hydrogels

The hydrogels of the invention may be used in various medical contexts. For example, in one implementation, the scope of the invention encompasses the use of the hydrogels described herein as topically applied wound-sealing glues. In such embodiments, the hydrogel may be tuned to have faster reaction kinetics (e.g., gelation being complete at 5-15 minutes) for example, by increasing the concentration of reactive groups or the concentration of reactant polymers in solution. In another implementation, the scope of the invention encompasses the use of the hydrogels described herein to fill subcutaneous wounds or other intracorporeal cavities, such as cuts, surgical incisions, etc. In such embodiments, the reactants may be tuned to gel at a slower rate (for example gelation being complete in 15-45 minutes) in order to allow the cross-linking mixture of complementary HA polymers to infiltrate the cavity completely and conform to the complex boundaries of such cavity before solidifying. In another embodiment, the invention encompasses the use of hydrogels described herein as replacement cartilage in wounded or degraded tissues. In another aspect, the invention comprises the formation of the hydrogels of the invention in molds, to create articles of manufacture with precise shape and dimensions, for example for use in medical implants, cell culture scaffolds, and other objects.

The methods of using the hydrogels disclosed herein may be applied to humans, for example human patients in need of wound care or other treatment, or to any other animal species, for example in veterinary or research contexts. The methods may also be applied in the ex vivo culture of biological materials, including microbes, cell cultures, and explanted tissues.

The hydrogel precursor solutions of the invention may be supplemented with various constituents to impart therapeutic or other properties to the resulting hydrogels. For example, the solutions may comprise antibiotics, anesthetics, growth factors, vitamins, cells (such as therapeutic stem cells), peptides and proteins, and small drug-Ike molecules.

Such compositions may be selected by one of skill in the art so as to be compatible with the reactive groups of the HA polymers, i.e., not substantially reacting with the reactive groups and interfering with gelation.

EXAMPLES

Example 1

Following is an exemplary implementation of the invention, demonstrating chemistries that enable biocompatible HA hydrogel formation with ideal kinetics and resulting hydrogels with desirable rheological properties for medical uses.

The hydrogels are formed by a "click" reaction between HA polymers functionalized with cyanobenzothiazole (CBT) and D-cysteine (D-Cys) to form novel and useful hydrogels. The reaction, occurs in fireflies and affords luciferin, which acts as the substrate for the light-producing enzyme luciferase. Unlike classic azide-alkyne click chemistry, this reaction does not require any catalyst and occurs in physiological conditions, or aqueous saline buffers in general, and is characterized by good kinetics (second-order rate constant $k_2 \sim 9$ $m^{-1}$ $s^{-1}$) and high yield.

In this example, the CBT-D-Cys "click" reaction is used to produce a binary HA-based system that affords a stable gel via in situ cross-linking with mild kinetics. To this end, two HA-based conjugates were created, one functionalized with CBT and one with D-Cys. The gelation kinetics, the rheological properties of the resulting gel, as well as its applicability as a filling or wound-sealing formulation were assessed. The rheological analysis conducted on both the reacting system and the fully formed gel confirmed both the mild kinetics of the sol/gel transition (~30 min) and the mechanical strength of the resulting 3-D network. A number of tests on porcine skin samples were also run. Injection and topical application of the binary HA mixture were performed to evaluate the amenability of the system to forming a subcutaneous gel phase or a diffused cross-linked phase throughout the various skin layers. Further, the mixture was applied on a model skin wound and the strength of the resulting sealant film was determined. Finally, both conjugates were incubated with epidermal keratinocytes to assay the safety of the disclosed system. The results strongly supported both the effectiveness and safety of the system and indicate its amenability for a variety of biomedical applications, such as treatment of skin disorders, wound healing, and cartilage replacement.

Materials and Methods. Hyaluronic acid (HA, MW=250K Da) was acquired from Creative PEGworks (Winston-Salem, N.C.). D-Cysteine, 6-amino-2-cyano-benzothiazole (ACBT), 1-Ethyl-3-[3-dimethylaminopropyl]carbodiimide hydrochloride (EDC), 1,2-diaminoethane (DAE), dimethylsulfoxide (DMSO) and ethanol were obtained from Sigma Aldrich (Saint Louis, Mo.). MES buffer, pH 4.5 and dextran desalting columns (MWCO=10 kDa) were obtained from Pierce (Rockford, Ill.). Full thickness porcine skin was purchased from Lampire Biological Laboratories (Pipersville, Pa.) and stored at −80° C. Human adult epidermal keratinocytes (HEKa cells) and all cell culture materials were acquired from Life Technologies (Grand Island, N.Y.).

Synthesis and Purification of HA-CBT and HA-D-Cys Conjugates. Hyaluronic acid was initially dissolved in 50:50 DMSO:MilliQ water at the concentration of 10 mg/mL through vigorous stirring and heating (60° C.) for 30 min. The solution was split in two aliquots, which were used for conjugation with CBT and D-Cys respectively. The first aliquot was activated by adding a 5 mg/mL solution of EDC in MES buffer (pH 4.5) to obtain a 6.5% molar ratio of EDC/carboxyl groups. After a short activation time (2 min), a 1 mg/mL solution of CBT in DMSO, pre-heated at 60° C., was added drop-wise to obtain a 6.5% molar ratio of CBT/carboxyl groups. The reaction was allowed to proceed overnight at 60° C. and under vigorous stirring. The second aliquot was similarly activated with EDC and reacted overnight with diaminoethane (DAE) at a 6.5% molar ratio. The resulting aminated HA was precipitated in ethanol and re-dissolved in warm ultrapure water (45° C.), again activated with EDC, and reacted with a solution of 1 mg/mL of D-Cysteine in MES buffer at a 6.5% molar ratio, overnight under vigorous agitation. After reaction, the HA-CBT and HA-D-Cys conjugates were twice precipitated in ethanol, re-dissolved in warm standard saline solution (45° C.) at approximately 20 mg/mL, and finally stored at 4° C. The yield of CBT and D-Cys coupling on HA was determined via differential balance by HPLC-RP analysis of the reaction supernatants.

Rheological characterization. The rheological experiments were performed with a rheometer AR-G2. The rheological flow and oscillatory experiments were performed using a Couette geometry (cup diameter=30.42 mm, gap=0.5 mm, and bob diameter and length of 27.95 mm and 42.15 mm, respectively). To prevent solvent evaporation, the material was thermally isolated (solvent trap) and the weight was checked before and after the experiment (difference in weights was less than 1%). All experiments were performed under constant temperature (37° C.). The gelation kinetics were monitored through time sweeping tests, and the storage G' and loss G" moduli were measured as function of time at 10 rad/s frequency and 1% stress strain. The HA-CBT and HA-D-Cys solutions were shortly pre-mixed (~5 min), loaded, and measured at the test temperature. Both frequency and flow sweeping tests were performed after the hydrogel formation. Frequency sweeping tests were conducted isothermally in the frequency range $0.01<\omega<100$ rad/s, while maintaining the stress strain at 1%. Normal force was maintained to a constant value as well, care was taken to ensure that residual stress due to loading was relaxed, and the hydrogel was allowed a soak time to equilibrate at the test temperature. The flow sweep experiments were made isothermally in the shear rate range $0.0005<\gamma<100$ $s^{-1}$, to determine the zero-shear viscosity and an intensive shear thinning regime. The data points were collected once every 100 s.

In situ (skin) internal and superficial gelation. Porcine skin samples were thawed at room temperature for 30 min prior to use, hair were clipped using scissors, and rinsed using 0.9% saline solution. Subcutaneous in situ gelation tests were performed by injecting an equimolar mixture of HA-CBT and HA-D-Cys solutions. The conjugates solutions at 2% w/w were combined to obtain a 5% mol concentration of both CBT and D-Cys, premixed for 3 min at room temperature under vigorous agitation, and finally injected (50 uL) using a 27 gauge needle. The skin samples were stored at room temperature in a Petri Dish for 1 hr to ensure complete gelation. The samples were sectioned using a scalpel in correspondence of the subcutaneous gel to obtain small (0.4 cm×0.4 cm) squares, which were frozen by immersion in a isopentane/dry ice bath, and stored at −80° C. Thin (20 μm) skin sections were obtained using a cryostat and imaged using an confocal microscope. Superficial gelation tests were also performed by sequentially applying HA-CBT and HA-D-Cys solutions (2% w/w) at a ratio of 1 mg of HA conjugate per cm² of skin. Skin samples were sectioned and imaged as described above.

Further, square porcine skin samples (2 cm×2 cm) were incised with a scalpel until reaching the underlying dermis layer. The incision was filled with an equimolar (5% mol) mixture of HA-CBT and HA-D-Cys conjugate solutions, both at 2% w/w, and the skin samples were incubated at 37° C. VETBOND™ Tissue Adhesive (3M) and PBS were used as positive and negative controls, respectively. Samples were analyzed visually and with a dynamometer to measure the strength needed to reopen the incision.

In vitro characterization of conjugates biocompatibility. Human adult epidermal keratinocytes (HEKa cells) were cultured in EPILIFE™ medium supplemented with Human Keratinocyte Growth Supplement, 50 U/mL penicillin, 50 μg/mL streptomycin, and 100 μg/mL neomycin. Cultures were grown at 37° C. with 5% $CO_2$. The cytotoxicity of HA and HA-conjugates was determined using the MTT Cell Proliferation Assay (ATCC, Manassas, Va., USA). Cells were seeded in 96-well microplates and allowed to attach overnight. Cells were incubated until ~80% confluency, at which time, media was removed and 250 μg/mL, 25 μg/mL, or 2.5 μg/mL HA or HA-conjugates in fresh media was added to the wells. Cells were incubated with test formulations overnight. Cells incubated with media only were used as a negative control. 5% SDS was used as a positive control. Wells with media only (no cells) was subtracted as the baseline. % Viability was determined according to the manufacturer's recommended protocol using a SAFIRE XFLUOR4™, V4.50 micro-plate reader (Tecan Group Ltd, Morrisville, N.Y.).

Results and Discussion. Preparation of the HA-CABT and HA-D-Cys conjugates and gelation chemistry. The polymer conjugates were prepared by aiming to obtain a concentration of functional groups (CBT and D-Cys) of 5%. CBT densities higher than 5% render the polymer conjugate less soluble or insoluble in water. According to the reaction 1:1 stoichiometry, it was attempted to obtain a conjugation of D-Cys to HA of 5% mol as well. The highest value of functional density compatible with water solubility was sought to ensure a good gelation yield. C18 RP-HPLC analysis of the reaction mixture and supernatants was performed to estimate the functionalization yield, and returned values of 4.7% and 5.3% mol. A qualitative analysis was initially performed to characterize the speed and yield of gelation between the two polymer conjugates. The liquid-phase "click" reaction between CBT and D-Cys, has been reported to afford high yields. As the 2% w/w aqueous solutions of HA-CBT and HA-D-Cys conjugates (5% mol) are mixed, the formation of cloudiness was observed. This is likely due to the formation of a thin solid interface between the two pure HA-CBT and HA-D-Cys liquid phases and comprising cross-linked polymer. If the slurry is vigorously stirred, the cloudiness dissolves and the cross-linking reaction proceeds until formation of a brightly yellow gel. On the other hand, if the cloudiness is not mechanically dissipated, it may persists as a milky suspension in the polymer solution and the gel may not form. This supports the hypothesis that the cloudiness consists of a locally precipitated cross-linked polymer, preventing further contact between the HA-CBT and HA-D-Cys liquid phases and thus interrupting the gelation process.

Rheological characterization. Oscillatory time sweep, gelation point: To study the gelation kinetics of the disclosed system, a mixture was prepared by combining an equimolar amount (5% mol, referring to CBT and D-Cys substitution levels on the HA chains) of 2% w/w solution of HA-CBT and HA-D-Cys conjugates in standard saline. The mixture was rapidly (~3 min) homogenized under vigorous stirring and poured into the Couette outer cylinder. The inner cylinder (bob) was lowered into the outer chamber until the polymer solution covered it completely. An oscillatory time sweep experiment was then performed to monitor the dynamic storage modulus G' and the loss modulus G" as functions of time. The resulting data shows the cross-over point (G'=G"), indicating gel formation, at 2,000 s. Throughout the measurement, the storage modulus increased for γ up to 10,000 s, to finally equilibrate at ~100 Pa.

Moderate gelation kinetics is favorable for the desired skin applications. An overly rapid gelation upon mixing would make the gel difficult to inject and would prevent the subcutaneous formation of a homogeneous network. On the other hand, an overly slow gelation and gel weakness (small G') would cause dispersion of the polymer due to diffusion throughout the skin layer, insufficient cross-linking, and ultimately prevent good tissue adhesion and consistence. The system was optimized to afford the right gelation time and a sufficient G' value. The hydrogel reached a well-developed network in less than 3 hr and was stable over time (one week) at 37° C. The initial dominance of G" over G' indicates a system characterized by the sol state, i.e. liquid-like behavior. As the system approaches the gelation point (G'=G"), the increase of the storage modulus is significantly faster than that of the loss modulus. The simultaneous growth of the moduli is due to the cross-linkage between the HA-CBT and HA-D-Cys conjugates, and that of G' particularly indicates an increase of the mechanical strength of the hydrogel. The crossover point (~2000 s) indicates the transition from the liquid to a solid phase, dominated viscoelastic behavior, and indicates the formation of a 3-D network typical of hydrogel obtained via chemical cross-linking. The network development provides a solid-like system, which imparts viscoelastic properties to the system. As the cross-linking accesses the final stage (~8,000 s), both G' and G" equilibrate and the formation of the network is well-developed. Notably, after the gelation point and as soon as G' exceeded G", the phase angle δ decreased rapidly. The hydrogel reached the onset of a plateau of the moduli in less than 3 hr with a small phase angle ~1°, which indicates a well-structured network controlled by the solid-like state. This was also confirmed by the moduli intensities that differed by almost two orders of magnitude.

Oscillatory frequency sweep, viscoelastic properties: The gel formed in the Couette rheometer was subsequently characterized via oscillatory frequency sweep analysis. The results indicate a G' higher than G" over the entire frequency range explored (0.01<ω<100 rad/s), with an average G'/G" ratio of about $10^2$, a behaviour characteristic of "strong gels". On the other hand, in "soft gels", such as soft tissues and biological gels, the moduli tend to show frequency dependence and the G'/G" ratio is typically lower than 10. The investigated system, due to the variability of the loss modulus, displayed hybrid characteristics, i.e. combined soft and strong gel properties.

Flow sweep, shear thinning behavior: In order to investigate the response of the preformed gel at different velocities, a flow sweep analysis was performed to measure the steady-state shear viscosity (η) as function of the shear rate γ. The results indicated a complex profile, characterized by a Newtonian plateau followed by a notable shear-thinning effect spanning over four orders of magnitude of η. In the shear-thinning regime, the viscosity profile was characteristic of a densely organized structure. The combination of the Newtonian plateau at low shear rates and shear thinning effect at intermediate and high shear rates, is common to biological gels, such as protein or polysaccharide based networks. The profile of η was modelled using the Carreau-Yasuda equation, which is commonly used for shear-thinning biological gels. The model describes the viscosity as $$\eta = \eta_\infty + (\eta_0 - \eta_\infty)[1 + (\lambda\gamma)^a]^{(n-1)/a} \quad \text{Equation 1}$$

wherein a, n, and λ are constant, empirically determined parameters. The parameter, a, adjusts the profile in the transition region, while n is the slope of the power law, with n<1 for shear-thinning and n>1 for shear-thickening behavior, respectively. The time constant λ defines the change from constant to power law profiles. The values of $\eta_0$ and $\eta_\infty$ describe the plateau at low and high shear rates, respectively. These viscosities give rise to the asymptotic limits of the model. Therefore, a, n, and λ control the behavior in the non-Newtonian regime between the two limits. In this case the plateau at high shear rates was missing, the model offers a good fitting of the experimental data. Linear regression of the collected data returned values of $\eta_0$=34686 Pa·s, $\eta_0$=0.16 Pa·s, λ=652 s, n=0.12, and a=64.

In situ (skin) internal and superficial gelation. Subcutaneous in situ gelation experiments were performed by injecting an equimolar (5% mol) combination of HA-CBT and HA-D-Cys conjugates in porcine skin. Following the results of the qualitative and rheological analysis of the gelation mechanism, it was decided to quickly premix the conjugate solutions (2% w/w) before injection in porcine skin. The skin samples were incubated at 37° C. for 1 hr to allow the cross-linking reaction to proceed to completion. A skin section was then cut in correspondence to the gelation area. To obtain a clean cross section of the skin samples and clearly visualize the polymer, gel samples were collected to obtain different cross sections of gel filling. Several 20 µm slices were imaged. Images were taken using an excitation wavelength of 405 nm and an emission filter centered at 560 nm with a 50 nm bandwidth. The areas with higher fluorescence overlap with the visually gel-filled areas, thus providing sufficient evidence of the subcutaneous gel formation.

Superficial gelation experiments were also performed by applying the conjugate solutions superficially on the skin samples. A 2% w/w HA-CBT solution was applied and allowed to penetrate in the skin layer for 15 min at 37° C. Subsequently, a 2% w/w HA-D-Cys solution was similarly applied. The skin samples were sectioned and imaged as described above. Extensive delivery of HA conjugates was observed. This was a surprising result given the size of the HA polymers (250 kDa). To verify that the transport observed here was not an artifact of the synthesis process, HA was conjugated to FITC in a similar fashion. HA-FITC polymer conjugates, however, did not penetrate into the skin. This suggests that either CBT or D-Cys, may play a role in the transport of HA into the skin. It is possible that CBT coupled to HA increases the overall polymer hydrophobicity, thus favoring penetration across the stratum corneum. Given its relatively high (5% mol) coupling on hyaluronic acid, these pendant groups could favor the polymer migration across the stratum corneum and into the epidermis Use of the gelating system as wound-repairing glue. The ability of the two HA conjugates to form a cross-linked wound-repairing film was estimated on a model skin incision. Porcine skin samples (2 cm×2 cm) were obtained and incised with a scalpel until reaching the underlying dermis layer. An equimolar (5% mol) mixture of HA-CBT and HA-D-Cys conjugate solutions, both at 2% w/w, was prepared as above described, and added until completely filling the incision (approx. 0.25 mL). The skin samples were then incubated at 37° C. to allow the cross-linking reaction to reach completion before being analyzed. The same procedure was performed using VETBOND™ Tissue Adhesive (positive control) and PBS (negative control). Upon visual inspection, the reaction between the polymer conjugates appeared to form a strong and homogeneous cross-linked film tightly connecting the wound extremities. Similar results were obtained with the VETBOND™ glue, while no connection was obtained with PBS as expected. Using a dynamometer, the ultimate tensile stress of intact skin and of skin repaired with either the polymer conjugate or VETBOND™ glue was measured, to determine the tension needed to needed to reopen the incision. A strength of about 25 MPa (~127 kg of weight, for a skin cross section of 0.5 $cm^2$) was needed to fracture the intact skin, which compares well with values of ultimate tensile stress reported in the literature. A strength of about 6.4 and 4.3 MPa (32 kg and 22 kg) was needed to reopen the incision repaired with VETBOND™ glue and our polymer conjugate.

Biocompatibility of HA-CBT and HA-D-Cys conjugates. To assess toxicity of HA-conjugates, HA, HA-CBT, and HA-D-Cys were incubated with HEKa cells overnight and % viability was determined. HEKa cells were used since keratinocytes are the primary cell-type in the skin, and therefore, represent a good estimate of the potential for skin irritation. Importantly, no cytotoxicity was observed for any of the conditions tested, while 5% SOS resulted in complete cell death, suggesting the HA conjugates of the invention are non-toxic to the skin.

Example 2. Use of HA Hydrogels for Drug Release

The conjugates solutions at 2% w/w were combined to obtain a 5% mol concentration of both CBT and D-Cys and premixed (3 min at room temperature) with a model protein to obtain a final protein concentration of 2 mg/mL. Two model proteins were utilised in this study, namely BSA and human IgG. A volume of 2 mL of mixture was allowed to gelate overnight in a cylindrical vial ($d_{in}$=1.27 cm). A volume of 5 mL of PBS, pH 7.4, was added to the vial and gently mixed with an agitator over 48 hours, without disrupting the gel/PBS interphase. 0.3 mL of solution were drawn every hour for the first 6 hours and subsequently every 6 hours, filtered with a centrifugal filter (MWCO=30 kDa) to remove non-protein species, and finally analysed via BOA assay to determine the protein concentration. As expected, the release of BSA was faster than that of IgG due to the notable difference in molecular weight, 66.5 kDa vs. 150 kDa, respectively. The rheological analysis of the gelating system indicated how to best perform the subcutaneous and superficial polymer application on the skin samples, especially the need of premixing in the first case and the subsequent application with intermediate time gap in the second one. Rheological studies indicated that the gel formed by CBT-D-Cys "click" chemistry affords a durable and well-developed gel with sufficient mechanical strength to withstand subcutaneous pressure. The G'/G" ratio and the value of viscosity (η) puts the system of the invention on par with other known in situ gelating systems, based on classical reactions, such as aldehyde-amine. Unlike these systems, however, the formulations of the invention showed high biocompatibility, as demonstrated by the analysis with HEKa cells, and does not give risk of unspecific reaction with the tissue surrounding the injected/diffused polymer. Mild reaction kinetics and good mechanical properties of the resulting gel demonstrate that the system of the invention is amenable to applications such as treatment of arthritis and tissue reconstruction, where the polymer filling is required to adjust perfectly within the cavity prior to gelation and high gel viscosity and durability is needed. The rheological data in combination with the in vitro characterization show the material can be used in zones where the moderate viscoelastic properties are well accepted, i.e. kidneys, pancreas, etc.

All patents, patent applications, and publications cited in this specification are herein incorporated by reference in their entirety to the same extent as if each independent patent, patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A system for forming a gel comprising,
   first and second functionalized hyaluronic acid ("HA") polymers, wherein:
   the first functionalized HA polymer comprises a first HA polymer moiety functionalized with a first reactive moiety that reacts with a second reactive moiety;
   the second functionalized HA polymer comprises a second HA polymer moiety functionalized with the second reactive moiety, which second reactive moiety comprises D-Cys or a D-Cys mimetic;
   wherein the first reactive moiety comprises CBT, a CBT mimetic, or another molecule that reacts with either the —SH or the —NH$_2$ group of D-Cys; and
   when the first and second functionalized HA polymers are brought together the first and second reactive moieties react to cross-link the functionalized polymers and form the gel.

2. The system of claim 1, wherein
   the first reactive moiety increases the hydrophobicity of the functionalized first polymer relative to unfunctionalized first polymer moiety.

3. The system of claim 2, wherein
   the second reactive moiety is or comprises D-Cys.

4. The system of claim 3, wherein
   the first reactive group is or comprises cyanobenzothiazole.

5. A method of forming a gel in situ in an intradermal site, the method comprising
   topically applying a first functionalized hyaluronic acid ("HA") polymer and a second functionalized hyaluronic acid ("HA") polymer;
   wherein the first functionalized HA polymer comprises a first HA polymer moiety functionalized with a first reactive moiety that reacts with a second reactive moiety;
   wherein the second functionalized HA polymer comprises a second HA polymer moiety functionalized with the second reactive moiety, which second reactive moiety comprises D-Cys or a D-Cys mimetic; and
   wherein at least the first functionalized HA polymer penetrates the skin, whereat its first reactive moiety reacts with the second reactive moiety, thereby cross-linking the first and second polymer moieties to one another.

6. The method of claim 5, wherein
   the first reactive moiety increases the hydrophobicity of the first polymer moiety.

7. The method of claim 6, wherein
   the first reactive moiety is or comprises CBT.

8. The method of claim 7, wherein
   the second reactive moiety is or comprises D-Cys.

9. The method of claim 5, wherein
   the first functionalized polymer and second functionalized polymers are applied to a wound.

10. The method of claim 5, wherein
    the first polymer and the second polymer react after transport across the stratum corneum.

11. The method of claim 5, wherein
    the first reactive moiety and the second reactive moiety form a cross-link which is fluorescent.

* * * * *